United States Patent
Atanassova et al.

(12) 
(10) Patent No.: US 6,313,282 B1
(45) Date of Patent: Nov. 6, 2001

(54) ISOLATED DNA SEQUENCE WHICH CAN SERVE AS TERMINATOR REGION IN A CHIMERIC GENE CAPABLE OF BEING USED FOR THE TRANSFORMATION OF PLANTS

(75) Inventors: Rossitza Atanassova, Strasbourg; Richard De Rose, Lyons; Georges Freyssinet, St Cyr Au Mont d'Or; Claude Gigot, Strasbourg; Michel Lebrun, Lyons, all of (FR)

(73) Assignee: Rhone-Poulenc Agrochimie, Lyons Cedex (FR)

( * ) Notice: Subject to any disclaimer, the term of this patent is extended or adjusted under 35 U.S.C. 154(b) by 0 days.

(21) Appl. No.: 08/896,771

(22) Filed: Jul. 18, 1997

Related U.S. Application Data

(63) Continuation of application No. 08/265,202, filed on Jun. 24, 1994, now abandoned.

(30) Foreign Application Priority Data

Jun. 25, 1993 (FR) .................................................. 93 08029

(51) Int. Cl.⁷ .............................. C07H 21/04; A01H 1/00
(52) U.S. Cl. ...................... 536/24.1; 536/23.6; 536/23.2; 800/288; 800/300; 800/287
(58) Field of Search ..................................... 800/300, 295, 800/288, 287; 536/24.1, 23.6, 23.2

(56) References Cited

FOREIGN PATENT DOCUMENTS 507698   10/1992   (EP) .

OTHER PUBLICATIONS

M.E. Chaboute, et al. (1988) "Polyadenylation of Histone H3 and H4 mRNAs in Dicotyledonous Plants" *Gene:* 71 217–223.

M.E. Chaboute, et al. (1987) "Genomic Organization and Nucleotide Sequences of two Histone H3 and Two Histone H4 Genes of Arabidopsis Thaliana"*Plant Mole. Biol.* 8: 179–191.

T. Nakayama, et al. (1989) "Cis–Acting Sequences that Modulate Transcription of Wheat Histone H3 Gene and 3' Processing of H3 Premature Messenger RNA" *Biol. Abstracts* 88:11 Abstract No. 119487.

R. Atanassova, et al. (1992) "A 126 bp Fragment of a Plant Histone Gene Promoter Confers Preferential Expression in Meristems of Transgenic Arabidopsis" *The Plant Journ.* 2:3 291–300.

M. Lepetit, et al. (1992) "A Plant Histone Gene Promoter Can Direct Both Replication–Dependent and —Independent Gene Expression in Transgenic Plants" *Mol. Gen. Genet.* 231 276–285.

N. Chaubet, et al. (1988) "The Histone H3 and H4 mRNAs are Polyadenylated in Maize" *Nucleic Acids Research* 16:4 1295–1304.

*Primary Examiner*—Gary Benzion
(74) *Attorney, Agent, or Firm*—Scully, Scott, Murphy & Presser

(57) ABSTRACT

Isolated DNA sequence which can serve as terminator region in a chimeric gene capable of being used for the transformation of plants 1) Chimeric gene for the transformation of plants.
2) It comprises at least, in the direction of transcription, a promoter region, a transgene and a terminator region, characterized in that the terminator region consists of at least one terminator region from a plant histone gene permitting the expression of the protein in the regions of rapid growth.
3) Production of transgenic plants.

18 Claims, No Drawings

ISOLATED DNA SEQUENCE WHICH CAN SERVE AS TERMINATOR REGION IN A CHIMERIC GENE CAPABLE OF BEING USED FOR THE TRANSFORMATION OF PLANTS

This application is a continuation application of U.S. application Ser. No. 08/265,202.

The present invention relates to the use of terminator regions isolated from plant transcribed genes, of new chimeric genes containing them and their use for the transformation of plants.

Numerous phenotypic characteristics associated with the expression of one or few gene elements can be integrated into the genome of plants and thus confer advantageous agronomic properties on these transgenic plants. In a non-extensive manner, there may be mentioned: the resistance to pathogenic agents for crops, the resistance to phytotoxic plant-protection products, the production of substances of food or pharmacological interest. In addition to the isolation and characterization of the gene elements encoding these various characters, an appropriate expression should be provided. This appropriate expression can be situated both at the qualitative and quantitative level. At the qualitative level, for example spacial level: preferential expression in a specific tissue, or temporal level: inducible expression. At the quantitative level, by the accumulated quantity of the product of expression of the gene introduced. This appropriate expression depends, for a large part, on the presence of regulator gene elements associated with transgenes, in particular as regards the quantitative and qualitative elements. Among the primordial elements providing this appropriate regulation, the use of homologous or heterologous, single or combined promoter regions has been widely described in the scientific literature. The use of terminator region downstream of the transgene has been used for the sole purpose of putting a boundary which makes it possible to stop the transgene transcription process, without presupposition as to their role in the quality or quantity of the expression of the transgene.

The present invention relates to the use of terminator regions isolated from plant transcribed genes, of new chimeric genes containing them and their use for the transformation of plants. It relates more particularly to the simultaneous use of terminator regions and promoters isolated from the same plant transcribed gene. It permits the appropriate expression, both quantitative and qualitative, of the transgenes under the control of these gene regulatory elements. This appropriate expression obtained by the use of the present invention may relate to characters such as: the resistance to pathogenic agents for crops, the resistance to phytotoxic plant-protection products and the production of substances of food or pharmacological interest. In particular, it makes it possible to confer an increased herbicidal tolerance on the transgenic plants by a preferential, qualitative and quantitative expression of the product of expression of the chimeric genes in the regions of the plant undergoing rapid growth. This specific appropriate expression of the gene for herbicidal resistance is obtained by the simultaneous use of the promoter and terminator region regulatory elements of the H4A748 histone gene from *Arabidopsis thaliana*. Such an expression pattern can be obtained for all the characters of interest, as described above, with the regulator elements used to confer an increased herbicidal tolerance. The present invention also relates to the plant cells transformed by means of these genes and the transformed plants regenerated from these cells as well as the plants derived from crossings using these transformed plants.

Among the plant-protection products used for the protection of crops, systemic products are characterized in that they are transported in the plant after application and, for some of them, accumulate in the parts undergoing rapid growth, especially the stem and root apexes, causing, in the case of herbicides, the deterioration, up to the destruction, of the sensitive plants. For some of the herbicides exhibiting this type of behaviour, the primary mode of action is known and results from an inactivation of characterized enzymes involved in the pathways of biosynthesis of compounds necessary for the correct development of the target plants. The target enzymes for these products can be located in various subcellar compartments and the observation of the mode of action of known products most often shows a localization in the plastidial compartment.

The tolerance of plants sensitive to a product belonging to this group of herbicides, and whose primary target is known, can be obtained by stable introduction into their genome of a gene encoding the target enzyme, of any phylogenetic origin, mutated or not as regards the characteristics of inhibition, by the herbicide, of the product of expression of this gene. Another approach consists in stably introducing into the genome of the sensitive plants a gene of any phylogenetic origin encoding an enzyme capable of metabolizing the herbicide into an inactive and non-toxic compound for the development of the plant. In this latter case, it is not necessary to have characterized the target of the herbicide.

Given the mode of distribution and accumulation of products of this type in the treated plants, it is advantageous to be able to express the product of translation of these genes so as to permit their preferential expression and accumulation in the regions of the plant undergoing rapid growth where these products accumulate. Furthermore, in the case where the target of these products is localized in a cellular compartment other than the cytoplasm, it is advantageous to be able to express the product of translation of these genes in the form of a precursor containing a polypeptide sequence permitting the tolerance-conferring protein to be addressed to the appropriate compartment, and in particular to the plastidial compartment.

As example illustration this approach, there may be mentioned glyphosate, sulphosate or fosametin which are broad-spectrum systemic herbicides of the phosphonomethylglycine family. They act essentially as competitive inhibitors, with respect to PEP (phosphoenolpyruvate), of 5-enolpyruvylshikimate-3-phosphate synthase (EPSPS, EC 2.5.1.19). After their application of the plant, they are transported into the plant where they accumulate in the parts undergoing rapid growth, especially the stem and root apexes, causing the deterioration, up to the destruction, of the sensitive plants.

EPSPS, the main target of these products is an enzyme of the pathway of aromatic amino acid biosynthesis which is localized in the plastidial compartment. This enzyme is encoded by one or more nuclear genes and synthesized in the form of a cytoplasmic precursor and then imported into the plastids where it accumulate in its mature form.

The tolerance of the plants to glyphosate and to products of the family is obtained by the stable introduction into their genome of an EPSPS gene of plant or bacterial origin, mutated or not as regards the characteristics of glyphosate inhibition of the product of this gene. Given the mode of action of glyphosate, it is advantageous to be able to express the product of translation of this gene so as to permit its high accumulation in the plastids and furthermore, in the regions of the plant undergoing rapid growth where the products accumulate.

It is known, for example according to U.S. Pat. No. 4,535,060, to confer on a plant a tolerance to a herbicide of the above type, in particular, N-phosphonomethylglycine or glyphosate, by introduction into the genome of the plants of a gene encoding an EPSPS carrying at least one mutation rendering this enzyme more resistant to its competitive inhibitor (glyphosate), after localization of the enzyme in the plastidial compartment. These techniques however need to be improved for a greater reliability in the use of these plants during a treatment by these products under agronomic conditions.

In the present description, "plant" is understood to mean any differentiated multicellular organism capable of photosynthesis and "plant cell" is understood to mean any cell derived from a plant and capable of constituting undifferentiated tissue such as calli, or differentiated tissue such as embryos or plant portions or plants or seeds. "Terminator region" is understood to mean an isolated DNA sequence of variable length, situated downstream of the coding part and corresponding to the structural part of a transcribed gene. Gene for tolerance to a herbicide is understood to mean any gene, of any phylogenetic origin, encoding either the target enzyme of the herbicide, having or otherwise one or more mutations with respect to the characteristics of inhibition by the herbicide, or an enzyme capable of metabolizing the herbicide into an inactive and non-toxic compound for the plant. Regions of the plant undergoing rapid growth is understood to mean the regions which are the site for substantial cellular multiplications, in particular the apical regions.

The present invention relates to the production of transformed plants having especially an increased tolerance to herbicides which accumulate in the regions undergoing rapid growth in the treated plants, by regeneration of cells transformed by means of new chimeric genes containing a gene for tolerance to these products. The subject of the invention is also the production of transformed plants having an increased tolerance to herbicides of the phosphonomethylglycine family by regeneration of cells transformed by means of new chimeric genes containing a gene for tolerance to these herbicides. The invention also relates to these new chimeric genes, as well as transformed plants which are more tolerant because of a better tolerance in the parts undergoing rapid growth in these plants, as well as the plants derived from crossings using these transformed plants. Its subject is also new terminator regions for the construction of the above chimeric genes.

More particularly, the subject of the invention is a chimeric gene for conferring on plants especially an increased tolerance towards a herbicide having EPSPS as target, comprising, in the direction of transcription, a promoter region, a transit peptide region, a sequence encoding an enzyme for tolerance to products of the phosphonomethylglycine family and a terminator region, characterized in that the terminator region consists of a fragment of a terminator region of a plant histone gene in any orientation relative to its initial orientation in the gene from which it is derived, permitting the preferential expression and the accumulation of the protein for herbicidal tolerance in the regions for accumulation of the said herbicide.

The histone gene, from which the terminator region according to the invention is derived, comes from a monocotyledonous plant such as for example wheat, maize or rice or preferably a dicotyledonous plant such as for example lucerne, sunflower, soya bean, colza or preferably *Arabidopsis thaliana*. The type H3 or preferably H4 histone gene is preferably used.

The transit peptide region comprises, in the direction of transcription, at least one transit peptide from a plant gene encoding an enzyme of plastidial localization, a part of the sequence of the N-terminal mature part of a plant gene encoding an enzyme of plastidial localization, then a second transit peptide from a plant gene encoding an enzyme of plastidial localization, preferably the ribulose-1,5-bisphosphate carboxylase/oxygenase (RuBisCO) small sub-unit gene according to European Patent Application/PCT 508 909. The role of this characteristic region is to permit the release, into the plastidial compartment, of a mature polypeptide with a maximum efficiency, preferably in native form.

The coding sequence which can be used in the chimeric gene according to the invention comes from a gene for herbicidal tolerance of any phylogenetic origin. This sequence may especially be that of the mutated EPSPS having a degree of tolerance to glyphosate.

The promoter region according to European Patent Application/PCT 507 698 can be of any origin, in single or duplicated form or combined with a gene which is expressed naturally in plants, that is to say, for example of bacterial origin, such as that of the nopaline synthase gene, or of viral origin such as that of the 35S transcript of the cauliflower mosaic virus, or preferably of plant origin such as that of the ribulose-1,5-bisphosphate carboxylase/oxygenase small sub-unit or preferably such as that of a plant histone gene and preferably of *Arabidopsis thaliana*. A type H3 or preferably H4 histone gene is preferably used.

The chimeric gene according to the invention may comprise, in addition to the above essential parts, an untranslated intermediate region (link) between the promoter region and the coding region as well as between the coding region and the terminator region which can be of any phylogenetic origin.

EXAMPLE 1

Construction of Chimeric Genes

The construction of chimeric genes according to the invention is carried out starting with the following elements:

1) Histone gene promoter: the promoter is isolated from a H4A748 histone clone of *Arabidopsis thaliana*, Strasburg, thesis, 1987 and M. E. Chaboute, University of Strasbourg, thesis, 1987 and M. E. Chaboute et al. (1987) Plant Mol. Biol. 8, 179–191). This promoter, comprising about 900 bp between the AvaI sites used to isolate it, was sub-cloned into the SalI site of pUCl8 available on catalogue (Pharmacia #27-4949-01) after filling the SalI and AvaI protruding ends using Klenow polymerase. One of the sub-clones obtained having the 5' end of the promoter close to the HindIII site of the pUCl8 polylinker and the 3' end of the promoter close to the XbaI site of the pUCl8 polylinker, was later used and was called prom.H4A748/AvaI/SalI-pUC18.

2) Transit peptide region: the two transit peptides as well as the mature protein elements used have been described, as well as their assembly (M. Lebrun et al., European Patent Application/PCT 508 909). This region comprises about 350 bp and is called Optimized Transit Peptide (OTP).

3) CT7 gene for herbicidal tolerance: it is derived from the mutated CT7 gene (Pro 101 to Ser) for EPSPS from *Salmonella thypymurium*, isolated by Stalker et al. (1985) J. Biol. Chem., 260, 4724–4728. The clone pGM34-2, provided by Calgene, was linearized with XbaI and then treated with *Vigna radiata* nuclease. After recutting with SmaI, the two blunt ends were ligated. The clone obtained had no NcoI site on the initiator ATG for translation, as well as a SalI site at 17 bp downstream of the stop codon. This clone was called pRPA-BL-104.

4) OTP/CT7 fusion: an expression cassette containing the optimized transit peptide (OTP) fused in the reading frame with the CT7 gene (B. Leroux et al., European Patent Application/PCT 507 698) is cloned into the vector pBSII SK (−) (Stratagene catalogue #212206). This 5'-OTP/CT7-3' cassette contains a XbaI site at its 5' end and an SstI site at its 3' end.

5) GUS reporter gene: it is a gene encoding the β-glucoronidase (GUS) present in the plasmid pBI 101-I available on catalogue (Clontech #6017-1).

6) Histone terminator region: it is isolated from the H4A748 histone gene from *Arabidopsis thaliana* (M. E. Chaboute, University of Strasbourg, thesis, 1987 and M. E. Chaboute et al. (1987) Plant Mol. Biol., 8, 179–191). A 661 bp Sau3AI fragment was isolated, rendered blunt-ended by treatment with Klenow polymerase and sub-cloned into the SmaI site of the phagemide pBluescript®II KS (+) available on catalogue (Stratagene #212207). The sequence of this fragment is presented below in the section: "sequence listing". It has been shown by S1 mapping that this isolated fragment comprises inside a 200 bp region of its 5' end, in the original direction of transcription, the sequence corresponding to that present before the polyadenylation site of the mRNA which is derived from the transcription of this gene. The nucleotide A in position 165 of the 661 bp sequence corresponding to the site of addition of the polyadenylated end present in the transcript (Chaboute M. E. et al. (1988) Gene, 71, 217–223). Two sub-clones were preserved, one of which has: the insert orientated in the original direction of transcription of the H4A748 gene in the form of an SstI-EcoRI fragment and called t-directH4A748/Sau3AI/SmaI-pKS, and the other, in the reverse direction, in the form of an SstI-EcoRI fragment and called t-inverseH4A748/Sau3AI/SmaI-pKS.

The sequence of 661 bp of the terminator region of *Arabidopsis thaliana* H4A748 histone in the original direction of transcription of the gene:

Res., 11, 369–385) present in the plasmid pBI 101-1 available on catalogue (Clontech #6017-I).

The assembling of all these elements was carried out in the following manner on the basis of the skeleton of the binary vector for the transformation of plants via *Agrobacterium tumefaciens*, pBI 101-1 available on catalogue (Clontech #6017-1):

Construction of pRA-1:

The H4A748 histone promoter from *Arabidopsis thaliana* was excised from the plasmid prom.H4A748/AvaI/SalI-pUC18 in the form of the HindIII/XbaI fragment of about 900 bp. This fragment was inserted, by ligation, into the plasmid pBI 101-1 digested with HindIII/XbaI. The recombinant plasmid obtained contains, in the direction of transcription of the chimeric gene: H4A748 promoter/GUS/nos terminator region and was called pRA-1.

Construction of pRA-2:

The H4A748 terminator region from *Arabidopsis thaliana* was excised from the plasmid t-directH4A748/Bau3AI/SmaI-pKS in the form of an SstI/EcoRI fragment of about 670 bp. This fragment was inserted, by ligation, in substitution for the nos terminator region after digestion of the plasmid pRA-1 with SstI/EcoRI. The recombinant plasmid obtained contains, in the direction of transcription of the chimeric gene: H4A748 promoter/GUS/H4A748 terminator region in direct orientation and was called pRA-2.

Construction of pRA-3:

The H4A748 terminator region from *Arabidopsis thaliana* was excised from the plasmid t-directH4A748/Bau3AI/SmaI-pKS in the form of an SstI/EcoRI fragment of about 670 bp. This fragment was inserted, by ligation, in substitution for the nos terminator region after digestion of the plasmid pRA-1 with SstI/EcoRI. The recombinant plasmid obtained contains, in the direction of transcription of the chimeric gene: H4A748 promoter/GUS/H4A748 terminator region in reverse orientation and was called pRA-3.

Construction of pRPA-RD-146:

The XbaI/SstI fragment of about 1.75 kbp containing OTP/CT7 was inserted, by ligation, in substitution for the

```
GATCCGCGTT TGTGTTTTCT GGGTTTCTCA CTTAAGCGTC TGCGTTTTAC TTTTGTATTG   60
GGTTTGGCGT TTAGTAGTTT GCGGTAGCGT TCTTGTTATG TGTAATTACG CTTTTTCTTC  120
TTGCTTCAGC AGTTTCGGTT GAAATATAAA TCGAATCAAG TTTCACTTTA TCAGCGTTGT  180
TTTAAATTTT GGCATTAAAT TGGTGAAAAT TGCTTCAATT TTGTATCTAA ATAGAAGAGA  240
CAACATGAAA TTCGACTTTT GACCTCAAAT CTTCGAACAT TTATTTCCTG ATTTCACGAT  300
GGATGAGGAT AACGAAAGGG CGGTTCCTAT GTCCGGGAAA GTTCCCGTAG AAGACAATGA  360
GCAAAGCTAC TGAAACGCGG ACACGACGTC GCATTGGTAC GGATATGAGT TAAACCGACT  420
CAATTCCTTT ATTAAGACAT AAACCGATTT TGGTTAAAGT GTAACAGTGA GCTGATATAA  480
AACCGAAACA AACCGGTACA AGTTTGATTG AGCAACTTGA TGACAAACTT CAGAATTTTG  540
GTTATTGAAT GAAAATCATA GTCTAATCGT AAAAAATGTA CAGAAGAAAA GCTAGAGCAG  600
AACAAAGATT CTATATTCTG GTTCCAATTT ATCATCGCTT TAACGTCCCT CAGATTTGAT  660
C                                                                 661
```

7) Terminator region "nos": this is a fragment containing the signal for the terminator region of the nopaline synthase (nos) gene of pTi37 (Bevan M. et al. (1983) Nucl. Acids.

GUS gene after digestion of the plasmid pRA-1 with XbaI/SstI. The recombinant plasmid obtained contains, in the direction of transcription of the chimeric gene: H4A748 promoter/OTP/CT7/nos terminator region and was called pRPA-RD-146.

Construction of pRPA-RD-147:

The XbaI/SstI fragment of about 1.74 kbp containing OTP/CT7 was inserted, by ligation, in substitution for the GUS gene after digestion of the plasmid pRA-2 with XbaI/SstI. The recombinant plasmid obtained contains, in the direction of transcription of the chimeric gene: H4A748 promoter/OTP/CT7/H4A748 terminator region in direct orientation and was called pRPA-RD-147.

Construction of pRPA-RD-148:

The XbaI/SstI fragment of about 1.74 kbp containing OTP/CT7 was inserted, by ligation, in substitution for the GUS gene after digestion of the plasmid pRA-3 with XbaI/SstI. The recombinant plasmid obtained contains, in the direction of transcription of the chimeric gene: H4A748 promoter/OTP/CT7/H4A748 terminator region in reverse orientation and was called pRPA-RD-148

EXAMPLE 2

Expression of the Activity of a Reporter Gene

1) Transformation and Regeneration

The vector is introduced into the non-oncogenic strain of *Agrobacterium tumefaciens* LBA 4404 available on catalogue (Clontech #6027-1) by triparental crossing by means of the "helper" plasmid pRK 2013 in *Escherichia coli* HB101 according to the procedure described by Bevan M. (1984) Nucl. Acids Res., 12, 8711–8721.

The technique for transformation starting with root explants from *Arabidopsis thaliana* L.-ecotype C24 was carried out according to the procedure described by Valvekens D. et al. (1988) Proc. Natl. Acad. Sci. USA, 85, 5536–5540. Briefly, 3 steps are necessary: induction of the formation of calli on Gamborg B5 medium supplemented with 2,4-D and kinetin; formation of buds on Gamborg B5 medium supplemented with 2iP and IAA; rooting and formation of seeds on hormone-free MS.

2) Measurement of the GUS Activity in the Plants a—histochemical observations

The revealing of the GUS activity (Jefferson R. A. et al., (1987), EMBO J., 6, 3901–3907) in various transgenic plant organs shows that the preferential expression in the meristematic regions is conserved with the constructs pRA-2 and 3. Furthermore, the construct pRA-2 makes it possible to observe an activity in the adult tissues (leaves, roots, spikes) which do not appear with the construct pRA-1.

b—fluorometric measurements

The GUS activity was measured by fluorometry on extracts of flower buds and leaves of the small rose (Jefferson R. A. et al. (1987) EMBO J., 6, 3901–3907) from 12 plants, corresponding to individual transformation events, for each of the constructs pRA-1, 2 and 3.

The accumulated mean results, in pmol MU/min.mg prot., are the following:

| Constructs | Leaves (L) | Buds (B) | B/L Ratios |
|---|---|---|---|
| pRA-1 | 850.25 | 3965.33 | 4.66 |
| pRA-2 | 4890.67 | 33683.75 | 6.89 |
| pRA-3 | 4211.73 | 27752.45 | 6.59 |

These measurements clearly show that the H4A748 terminator region, in direct or reverse direction, induces an increase in the activity of the expression of the chimeric gene, in particular in the regions of the plant undergoing rapid growth.

EXAMPLE 3

Tolerance of Transgenic Plants to a Herbicide

1) Transformation and Regeneration

The vector is introduced into the non-oncogenic strain of *Agrobacterium tumefaciens* LBA 4404 available on catalogue (Clontech #6027-1) by triparental crossing by means of the "helper" plasmid pRK 2013 in *Escherichia coli* HB101 according to the procedure described by Bevan M. (1984) Nucl. Acids Res., 12, 8711–8721.

The transformation technique starting with tobacco foliar explants is based on the procedure described by Horsh R. et al. (1985) Science, 227, 1229–1231. The regeneration of the PBD6 tobacco (source SEITA-France) from foliar explants is carried out on an Murashige and Skoog (ME) base medium comprising 30 g/l of saccharose as well as 200 $\mu$g/ml of kanamycin in three successive steps: the first comprises the induction of shoots on an MS medium supplemented with 30 g of saccharose containing 0.05 mg of naphthylacetic acid (NAA) and 2 mg/l of benzylaminopurine (BAP) for 15 days. The shoots formed during this step are then developed by culture on an MS medium supplemented with 30 g/l of saccharose but containing no hormone, for 10 days. Then the developed shoots are collected and they are cultivated on a one-half diluted MS rooting medium containing half the content of salts, vitamins and sugars and containing no hormone. After about 15 days, the rooted shoots are planted in the soil.

2) Measurement of the Tolerance to Glyphosate

Twenty transformed plants were regenerated and transferred into a greenhouse for each of the constructs pRPA-RD-A, B and C. These plants were treated in a greenhouse at the 5-leaf stage with an aqueous suspension of RoundUp corresponding to 0.8 kg of glyphosate active material per hectare. The results correspond to the observation of phytotoxicity values noted 3 weeks after treatment. Under these conditions, it is observed that the plants transformed by the constructs exhibit on average an acceptable tolerance (pRPA-RD-146) or even a good tolerance (pRPA-RD-147 and 148 ) whereas the non-transformed controlled plants are completely destroyed. These results show clearly the improvement provided by the use of a chimeric gene according to the invention for the same gene encoding the tolerance to glyphosate.

The transformed plants according to the invention can be used as parents for the production of lines and hybrids having the phenotypic character corresponding to the expression of the introduced chimeric gene.

What is claimed is:

1. An expression cassette for expression of a chimeric gene in plants, comprising in the direction of transcription, a DNA sequence for at least one terminator region of an *Arabidopsis thaliana* histone H4748 gene in direct or reverse orientation relative to the H4748 gene from which it is derived, wherein said terminator region regulates the expression of the chimeric gene.

2. A chimeric gene for the transformation of plants comprising, in the direction of the transcription, a promoter region, a sequence of a gene for herbicide tolerance and a terminator region, wherein the terminator region comprises a sequence according to claim 1.

3. A chimeric gene according to claim 2 wherein the promoter region is obtained from the same Arabidopsis histone gene as the terminator region.

4. A chimeric gene according to claim 2 wherein the promoter region comprises a duplicated plant histone promoter.

5. A chimeric gene according to claim 2 wherein the promoter region comprises at least one promoter of an Arabidopsis histone gene associated with a different promoter derived from a gene which can be expressed in plants.

6. A chimeric gene according to claim 2 wherein the sequence of a gene for herbicide tolerance makes it possible to confer on the plants an increased tolerance to a herbicide.

7. A chimeric gene according to claim 6, wherein the gene for herbicide tolerance is fused with a DNA sequence encoding a transit peptide region permitting the accumulation of the product of translation of the gene for herbicide tolerance in a subcellular compartment.

8. A chimeric gene according to claim 7, wherein the transit peptide region permits the accumulation of the product of translation of the gene for herbicide tolerance in a plastidial compartment.

9. A chimeric gene according to claim 7, wherein the transit peptide region comprises, in the direction of transcription, at least one transit peptide from a plant gene encoding an enzyme of plastidial localization, a part of the sequence of the N-terminal mature part of a plant gene encoding an enzyme of plastidial localization, and a second transit peptide from a plant gene encoding an enzyme of plastidial localization.

10. A chimeric gene according to any one of claims 2 to 9, wherein the gene for herbicide tolerance encodes an enzyme capable of metabolizing the herbicide into an inactive and non-toxic compound of the plant.

11. A chimeric gene according to claim 10, wherein the gene for herbicide tolerance encodes an enzyme with increased tolerance to N-phosphonomethylglycine (GLYPHOSATE).

12. A chimeric gene according to claim 10, wherein the gene for herbicide tolerance is of any phylogenetic origin.

13. A vector for the transformation of plants, wherein the vector comprises a chimeric gene according to claim 10.

14. A strain of Agrobacterium sp., comprising a vector according to claim 13.

15. A transformed plant cell, comprising a chimeric gene according to claim 10.

16. A transformed plant obtained from a cell according to claim 15.

17. The chimeric gene of claim 2 wherein the expression of a gene for herbicide tolerance is localized in the regions for accumulation of said herbicide in plants.

18. A 3' termination region isolated from an *Arabidopsis thaliana* histone H4 gene and having the nucleotide sequence as set forth in Sequence ID NO: 1.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 661 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
GATCCGCGTT TGTGTTTTCT GGGTTTCTCA CTTAAGCGTC TGCGTTTTAC TTTTGTATTG      60

GGTTTGGCGT TTAGTAGTTT GCGGTAGCGT TCTTGTTATG TGTAATTACG CTTTTTCTTC     120

TTGCTTCAGC AGTTTCGGTT GAAATATAAA TCGAATCAAG TTTCACTTTA TCAGCGTTGT     180

TTTAAATTTT GGCATTAAAT TGGTGAAAAT TGCTTCAATT TTGTATCTAA ATAGAAGAGA     240

CAACATGAAA TTCGACTTTT GACCTCAAAT CTTCGAACAT TTATTTCCTG ATTTCACGAT     300

GGATGAGGAT AACGAAAGGG CGGTTCCTAT GTCCGGGAAA GTTCCCGTAG AAGACAATGA     360

GCAAAGCTAC TGAAACGCGG ACACGACGTC GCATTGGTAC GGATATGAGT TAAACCGACT     420

CAATTCCTTT ATTAAGACAT AAACCGATTT TGGTTAAAGT GTAACAGTGA GCTGATATAA     480

AACCGAAACA AACCGGTACA AGTTTGATTG AGCAACTTGA TGACAAACTT CAGAATTTTG     540

GTTATTGAAT GAAAATCATA GTCTAATCGT AAAAAATGTA CAGAAGAAAA GCTAGAGCAG     600

AACAAAGATT CTATATTCTG GTTCCAATTT ATCATCGCTT TAACGTCCCT CAGATTTGAT     660

C                                                                     661
```